United States Patent [19]

Barth

[11] Patent Number: 4,538,315
[45] Date of Patent: Sep. 3, 1985

[54] DENTAL HYGIENE APPARATUS HAVING A PLURALITY OF ROTATING BRUSHES

[76] Inventor: Frédéric Barth, 11, Place du Marché, Chevry II, 91190 Gif-sur-Yvette, France

[21] Appl. No.: 524,062

[22] Filed: Aug. 17, 1983

[51] Int. Cl.³ .............................................. A46B 13/02
[52] U.S. Cl. ...................................... 15/23; 15/22 R; 15/24
[58] Field of Search ............................... 15/22, 23, 24; 128/62 R, 62 A

[56] References Cited

U.S. PATENT DOCUMENTS

| 2,628,377 | 2/1953 | Cockriel | 15/23 |
| 4,048,690 | 9/1977 | Wolfson | 15/22 R |
| 4,224,710 | 9/1980 | Solow | 15/22 R |

FOREIGN PATENT DOCUMENTS

| 1286504 | 1/1969 | Fed. Rep. of Germany | 15/23 |
| 2115909 | 6/1972 | Fed. Rep. of Germany | |
| 502794 | 3/1971 | Switzerland | 15/23 |
| 1118699 | 7/1968 | United Kingdom | 15/23 |

Primary Examiner—Edward L. Roberts
Attorney, Agent, or Firm—Beveridge, DeGrandi & Weilacher

[57] ABSTRACT

A dental hygiene apparatus having five incurvated, flexible, rotating brushes mounted in a H-shaped arrangement on a housing which comprises an open brush holder portion matching with two opposed half dental arches and consists of an outer cheek-guard and an inner tongue-guard, and a closed biting portion provided with a pair of opposite restrictions for receiving the incisor teeth of the other two half dental arches.

9 Claims, 13 Drawing Figures

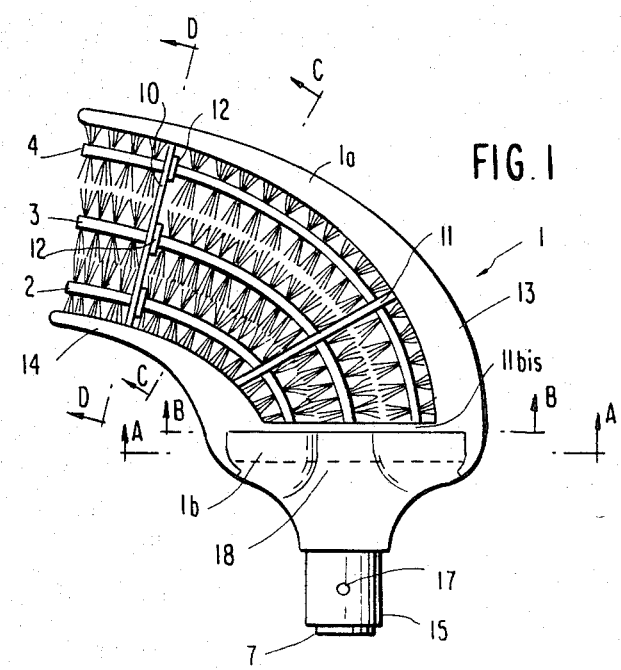
FIG. 1
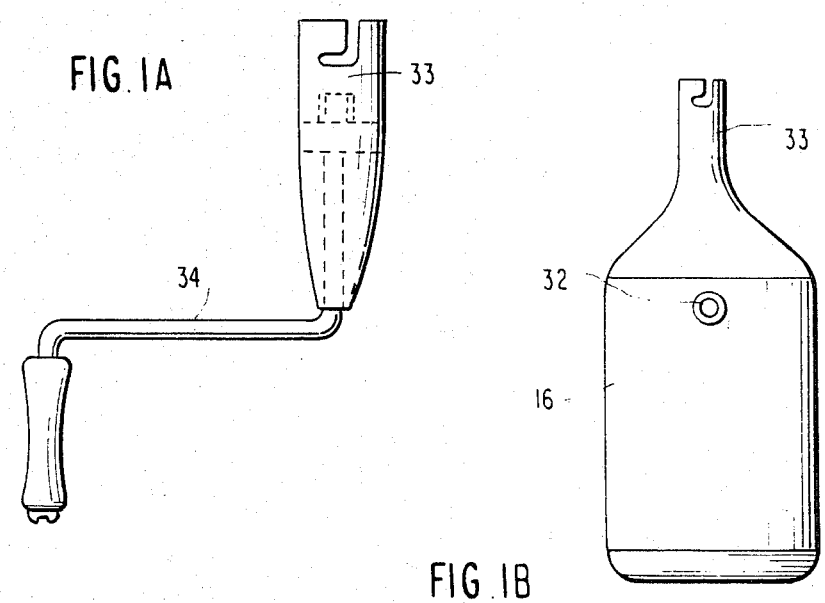
FIG. 1A
FIG. 1B

DENTAL HYGIENE APPARATUS HAVING A PLURALITY OF ROTATING BRUSHES

This invention relates to a dental hygiene apparatus having a plurality of incurvated, either flexible or hinged, rotating brushes, which are rotatively driven so as to simultaneously clean the teeth of the two opposed mandibles by brushing in the gum-tooth direction.

Daily tooth brushing is usually carried out with hand-operated toothbrushes the working portion of which is to be moved from one dental surface to another. With all such brushes, the user must consider the movements he or she has to impart to the brush and despite such consideration some dental surfaces may receive inadequate brushing or be missed altogether. Thus brushing is rendered tedious or incomplete.

It has previously been suggested to replace hand-operated tooth-brushes by a dental hygiene apparatus having a plurality of rotating brushes.

Some of these apparatus include a pair of brushes rotating in opposite directions and adapted to simultaneously brush the same sides (inner or outer side) of one or more opposed teeth (i.e of the upper mandible and the lower mandible). This type of apparatus has multiple drawbacks. In particular, upon transition from brushing the outer sides of the teeth to brushing the inner sides of the teeth, and vice-versa, the direction of rotation of the brushes must be reversed in order to continue brushing the teeth in the proper gum-tooth direction. In addition, while simultaneous brushing of the outer sides of opposed teeth is feasible with such an apparatus, simultaneous brushing of the inner sides of opposed teeth is practically impossible because the user must unclench his or her teeth to gain access to the inner side of the teeth. Finally, such an apparatus is to be moved within the mouth between the end teeth of the mandibles.

Other apparatus include either two or three rotating brushes to simultaneously brush the inner and outer sides and, if desired, the occlusal or morsal side of one or more teeth of the mandible. In such an apparatus, the brushes can continuously rotate in the same direction. However, it remains necessary to move the apparatus over all the teeth, and it is difficult to move the apparatus within the mouth, over both dental arches, inasmuch as the rectilinear shape of the three brushes of such an apparatus does not match the incurvated shape of dental arches.

Another apparatus aims to overcome the above drawbacks by using a pair of incurvated brushes having a length and shape matching the length and shape of dental arches for simultaneous brushing of the inner and outer sides of all teeth of the opposed mandibles. However, this apparatus is quite cumbersome. Thus, its introduction into the mouth of a particular user appears very uncomfortable or even impossible. Indeed, the drive for the four brushes is provided at one end of the apparatus, i.e. in the back area of two opposed half-mandibles. For morphological reasons, positioning of such a drive in the back area of two opposed half mandibles results in the user's inability to clench his or her teeth while the apparatus is within the mouth. It should also be noted that the four brushes of this apparatus allow only brushing of the inner and outer sides of the teeth but not of the occlusal sides. Finally, since the apparatus must match the shape of both opposed dental arches, adaptation to dental arches having different sizes and configurations is not possible. As much, manufacture of a substantial number of models differing both in size and shape would apparently be necessary.

Finally, an apparatus has been suggested that is adapted to simultaneously clean all the teeth of either a single dental arch or of two opposed dental arches by means of groups of three brushes, having alternating axial rather than rotational movement. In this apparatus, one of the brushes extends in an orthogonal direction with respect to the occlusal side and the other two brushes extend at an angle of 45° with respect to the inner and outer sides of the teeth. In addition to the obvious complexity and low strength of the brushing system of such an apparatus, another disadvantage is to be noted. While positioned at 45° with respect to the inner and outer sides of the teeth, the brush hair can disintegrate the dental or bacterial plate, however, it cannot remove the same. In addition, this movement of the inner and outer brushes may give rise to gingival inflammation as a result of mechanical traumatisms in the area of the gum-tooth groove, which, in turn, may result in a gingival recession.

The present invention is directed to a dental hygiene apparatus which is compact, has simple and reliable construction and which can be used without any danger for effective, complete and quick cleaning of all the tooth sides, while it is adaptable to dental arches having various sizes and configurations.

The dental hygiene apparatus in accordance with the invention has five incurvated brushes mounted in a H-shaped arrangement, wherein the axes of four brushes are disposed at the four ends of the H and the axis of the fifth brush is disposed at the center point of the H horizontal leg. The axes of the brushes are disposed upon a housing which includes an open brush holder portion in the shape of an arcuate sector having a length and an incurvated shape substantially matching with two opposed half dental arches. Said portion consists of an outer cheek-guard and an inner tongue-guard opposite to each other, between which a lower continuous opening and an upper continuous opening in opposition to each other over the whole length of the brushes are provided. Said cheek-guard and tongue-guard are connected to each other by at least two transverse spacers acting as mounting supports for the brushes. Said housing further includes, in alignment with the drive end of the brushes, a closed biting portion defining a pair of opposite upper and lower restrictions for receiving, when the apparatus is within the mouth between two opposed half dental arches, the upper and lower incisor teeth of the other two opposed half dental arches to lock the apparatus in the mouth by biting in the area of said restrictions.

The five incurvated brushes mounted in a H arrangement ensure simultaneous brushing of the inner, outer and occlusal sides of the opposite teeth of both dental arches. The brushes extend over a distance equal to the length of a half dental arch so that the apparatus effects simultaneous brushing of all the teeth of two opposed half dental arches. Once these teeth have been brushed, the user only has to rotate the apparatus by 180° and to then introduce it between the teeth of the other two opposed half dental arches without need to change the direction of rotation of the brushes. The cheek-guard and the tongue-guard prevent any danger of traumatism by the rotating brushes. Since the brushes are driven from the housing end located in the front area of the mouth, at the incisor teeth level, the user can easily bite the apparatus with his or her incisor teeth. The two restrictions provided in the housing for receiving the incisor teeth automatically ensure the proper positioning of the apparatus within the mouth.

The five brushes of the apparatus may be driven, for example by an electrical motor through a set of seven or preferably nine gears with a center gear being driven directly by the motor shaft. These gears may be located in the apparatus housing in the area of the restrictions permitting biting by the incisor teeth. The brush holder portion can be shaped as an arcuate sector and the biting portion can be made either as a single piece or as two separate pieces which can be coupled to and uncoupled from each other.

However, it is also possible, instead of providing the gear train in the housing, to provide it in a handle containing the electrical motor and to provide it with capability to be coupled with and uncoupled from the housing. In this case, the connection between the gear train and the five brushes may be provided by five flexible shafts, e.g. multi-strand metal cables or plastic rings including quick connection means.

It is also possible to drive the five brushes through five turbines fed with fluid from a pressure fluid source. In addition, it is possible to drive the five brushes from a center shaft through pulleys and belts.

Preferably, the brushes have hair elements of various lengths such as alternating long and short hair elements. By this means, it is possible to compensate for morphological and/or orientation differences.

The apparatus in accordance with the present invention, when viewed in transverse cross-section with respect to a vertical axis passing through the axis of the center brush, has an assymetrical shape as concerns the restrictions for receiving the upper and lower incisor teeth, the position of the axes of the other brushes and the height of the tongue-guard and the cheek-guard. Such assymetry prevents the housing from interfering with the bunoid papillas of the user and allows brushing of the entire height of the upper incisor teeth, the outer side of which is higher than the inner side.

On the other hand, the apparatus in accordance with the invention is exactly symmetrical with respect to a horizontal middle plane passing through the axis of the center brush in order to provide identical brushing action in both positions to correspond with brushing of both the left and right half dental arches.

With reference to the accompanying drawings, several illustrative but not limitative embodiments of a dental hygiene apparatus in accordance with the invention will be described in more detail hereinafter; in the drawings:

FIG. 1 is a top view of a preferred embodiment of the apparatus in accordance with the invention;

FIG. 1A is an elevational view of a handle for attachemnt to and driving of the apparatus;

FIG. 1B is an elevational view of an electrical motor-reducer gear for attachment to and driving of the apparatus;

Figure 2:
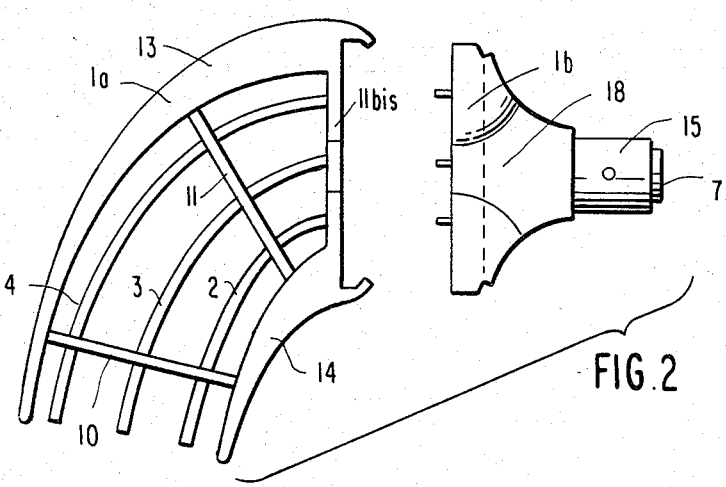
FIG. 2 is a diagrammatic top view of the apparatus of FIG. 1, in which the housing is shown broken apart into two portions.

The dental hygiene apparatus as shown in FIGS. 1 to 8 includes a housing 1 consisting of two portions 1a and 1b which can be coupled to each other (FIG. 1) and uncoupled from each other (FIG. 2).

Figure 6:
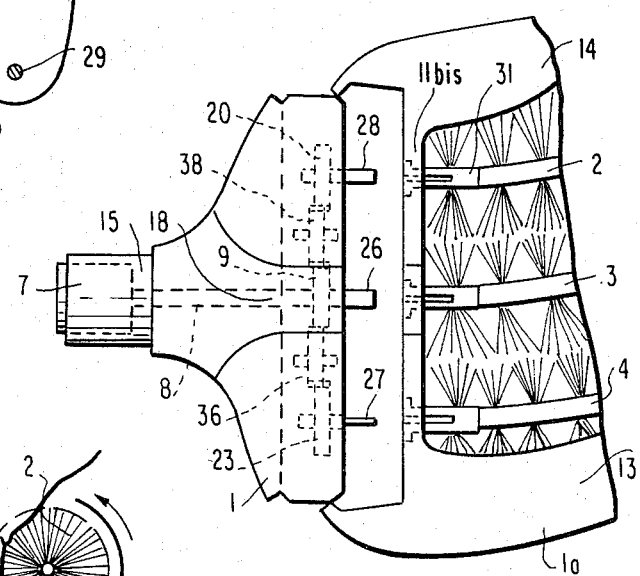
FIG. 6 is a partially broken-away top view, on an enlarged scale, showing the disunited two housing portions.
Figure 7:
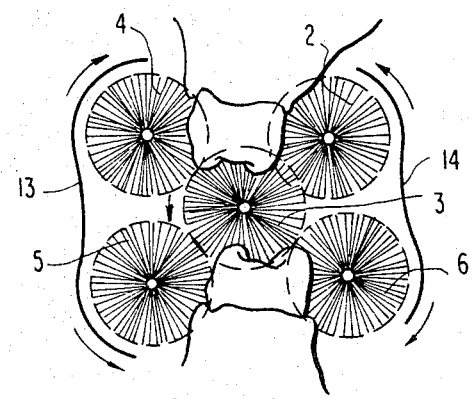
FIG. 7 is a cross-section along C—C of FIG. 1, wherein the apparatus is within the mouth.
Figure 8:
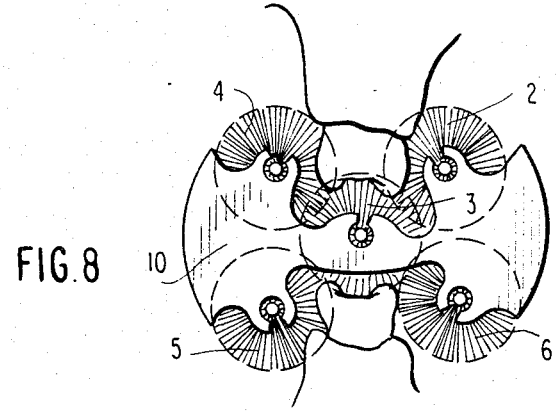
FIG. 8 is a cross-section along D—D of FIG. 1, wherein the apparatus is within the mouth.

As best shown in FIGS. 7 and 8, five brushes 2, 3, 4, 5 and 6 arranged in a H shape are rotatably mounted on the brush holder portion 1a. The five brushes 2 to 6 are rotatably mounted on three supports 10, 11, 11 bis, one of which (10) is shown in FIG. 8. Brushes 2 through 6 are fixedly secured in the axial direction at one end thereof in support 11 bis (see FIG. 6) and are each provided with a thrust washer 12 bearing on the support 10 at their other end.

Supports 10, 11 and 11 bis are integral with opposing cheek-guard 13 and tongue-guard 14. Cheek-guard 13 and tongue-guard 14 are disposed outwardly and in opposition along the two sides of the set of brushes corresponding to the vertical legs of the H (as best shown in a FIG. 4).

Figure 3:
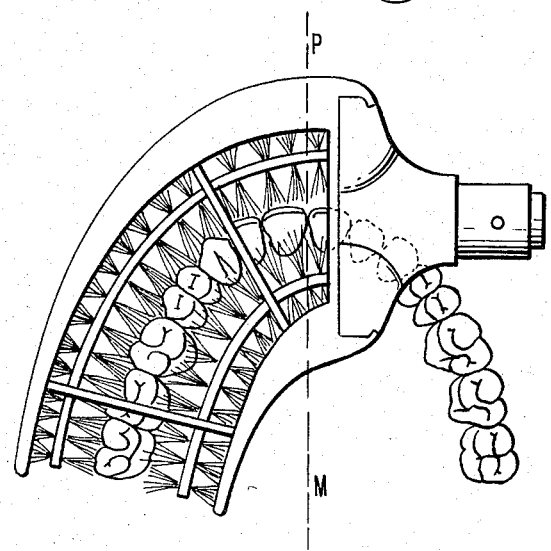
FIG. 3 is a partial top view of the apparatus of FIG. 1, showing the position of the apparatus with respect to an arch to be brushed.

The tegument-guards 13 and 14 and the brushes 2, 3, 4, 5, 6 each have an incurvated shape and a length substantially matching the length of a half dental arch (see FIG. 3).

Brushes 2 to 6 are each provided with a flexible axis or hub allowing the brushes to rotate about their axes while retaining the incurvated shape imparted thereto by tegument-guards 13 and 14, through supports 10, 11 and 11 bis.

The housing portion (biting portion) 1b contains a gear train which will be described hereinbelow. At its end opposite to the one by which it can be coupled to the housing portion 1a, it is provided with a ring for connecting to a locking teat 17. One end 7 of the drive shaft of the gear train coaxially extends beyond housing portion 1b and connecting ring 15. Connecting ring 15 and end 7 of the drive shaft permit the apparatus to be functionally connected either to a crank 34 or to an electrical motor-reducer gear 16 having an on-off switch 32. Both crank 34 and motor-reducer gear 16 are provided with a female connecting portion 33 for coupling with connecting ring 15 in bayonet-lock fashion, whereby drive connection between the output shaft of crank 34 or motor-reducer gear 16 and end 7 of input shaft 8 of the gear train contained in housing portion 1b becomes effective when the members 15 and 33 are locked with each other.

FIG. 2 shows the two housing portions 1a and 1b uncoupled from each other. The purpose of such an uncoupling is to permit easy change of the brushes, i.e. of housing portion 1a on which the brushes are mounted.

FIG. 3 illustrating the apparatus riding on a half dental arch, clearly shows that both the length and shape of the brushes and the tegument-guards substantially match with a half dental arch. Dotted line PM in FIG. 3 illustrates the dental "middle sagittal plane", i.e. a plane vertically passing through the center point of a dental arch so as to divide the arch into a pair of symmetrical half arches.

It should be noted that the cheek-guard 13 has an increased height in the lip area. Also, tongue-guard 14 has, over its entire length, a lower height than cheek-guard 13.

Figure 4:
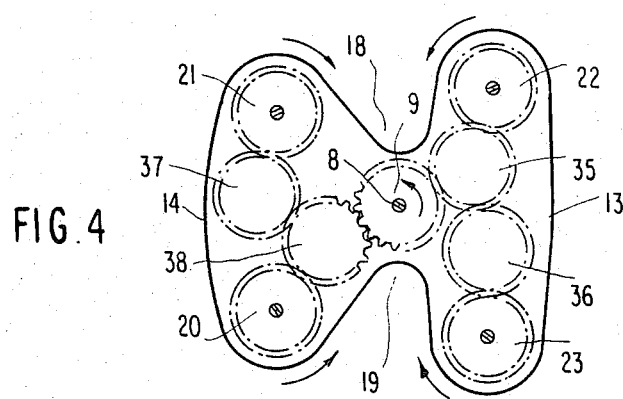
FIG. 4 is a cross-section along A—A of FIG. 1.
Figure 5:
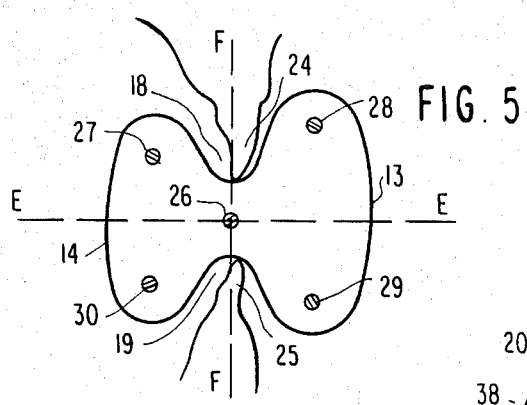
FIG. 5 is a cross-section along B—B of FIG. 1.

As shown in FIGS. 4 and 5, the apparatus has an asymmetrical construction with respect to a vertical axis FF passing through the axis of center brush 3. On the other hand, the apparatus has a symmetrical construction with respect to a horizontal plane EE passing through the axis of center brush 3.

As also shown in FIGS. 4 and 5, housing portion 1b is provided with a pair of opposite restrictions, namely an upper restriction 18 and a lower restriction 19. FIGS. 4 and 6 illustrate the gear train mounted within housing portion 1b. The gear train includes a center gear 9 rotatably fixed to input shaft 8, the end 7 of which provides connection with the crank or the motor-reducer gear. Center gear 9 is in meshing engagement with two gears 35 and 38. Gear 35 is in direct meshing engagement with a gear 22, and through an intermediate gear 36, with a gear 23. Likewise, gear 38 is in direct meshing engagement with a gear 20, and through an intermediate gear 37, is in meshing engagement with a gear 21. Gears 9, 20, 21, 22 and 23 are disposed, like brushes 2 to 6, in a H-fashion, so that center gear 9 is located at the center point of the horizontal leg of the H, gears 20 and 21 at each end of one vertical leg and gears 22 and 23 at each end of the other vertical leg of the H. The purpose of the gear train is to provide, when center gear is driven in one direction, namely counterclockwise in FIG. 4, rotation of gears 20 and 22 in the same direction as gear 9, i.e. counterclockwise, and rotation of gears 21 and 23 in the opposite direction.

It should be noted that center gear 9 is located in the center point between restrictions 18 and 19 of housing portion 1b.

In FIG. 6 showing the two housing portions 1a and 1b in their uncoupled position, ends 26, 27 and 28 at the output side of the axes of gears 9, 20, and 23 are clearly shown. Ends 29 and 30 at the output side of the axes of gears 21 and 22 are hidden from view in FIG. 6. These ends extend beyond housing portion 1b and are shaped so as to permit disengageable drive connection with the hubs of brushes 2 through 6, respectively. To such effect, as shown in the drawing, axes ends 26, 27, 28, 29 and 30 may consist of flat male connecting parts adapted to become nested within female connecting parts 31 provided at the drive ends of the hubs of brushes 2 to 6.

When the apparatus is introduced into the mouth between two opposite half dental arches (see FIG. 3), incisor teeth 24 and 25 (FIG. 5) of the other two opposite half dental arches engage restrictions 18 and 19 of housing portion 1b. As shown in FIGS. 7 and 8, the molars (as well as the premolars, canine and incisor teeth) of the opposite half dental arches to be cleaned come into place in two arcuate cleaning pathways, namely an upper and a lower pathway, which are defined by brushes 2, 3 and 4 and brushes 3, 5 and 6, respectively. The direction of rotation of the brushes is pre-selected so that the four end brushes (2, 4, 5 and 6) rotatingly brush the teeth in the gum-tooth direction as shown in FIG. 7. The four end brushes thus provide brushing of the inner and outer sides of all the teeth of the two opposite half arches, while the center brush 3 provides brushing of the occlusal sides of the upper and lower teeth thereof.

Due to the symmetrical construction of the apparatus with respect to plane FF (FIG. 5), the brushes assume exactly the same disposition with respect to the teeth of the other two opposite half dental arches when the apparatus has been rotated by 180° and introduced between the other two opposite half dental arches. The direction of brushing from the gums to the teeth is kept without reversal of the direction of rotation of the brushes.

Figure 9:
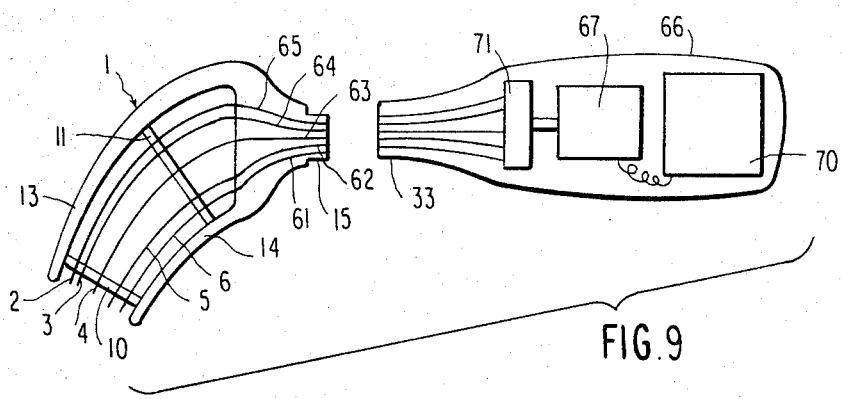
FIG. 9 is a diagrammatic view of another embodiment of the apparatus in accordance with the invention.

FIG. 9 illustrates a modified embodiment of the apparatus in accordance with the invention in which the housing assembly 1 has a unitary construction. Herein, brushes 2, 3, 4, 5 and 6 are driven by five flexible multi-strand metal cables or plastic rods 61, 62, 63, 64 and 65 which may be in alignment with the brush hubs and the ends of which terminate into connecting ring 15. The latter is adapted to cooperate with a connecting female part 33 of a handle 66 containing an electrical motor 67 powered by a power supply 70. The output shaft of the motor is provided with a gear train 71 similar to the one shown in the previous embodiment. However, instead of being mounted on the housing, herein the gear train is contained in the handle 66 and fixed to five cables or rods similar to those mounted on housing 1 and terminating into connecting part 33. Coupling between the cables or rods of housing 1 and handle 66 is provided by conventional connecting means, such as the means used in the previous embodiment to provide connection between the output shafts of gears 9, 20, 21, 22, 23 and the brush hubs.

Figure 10:
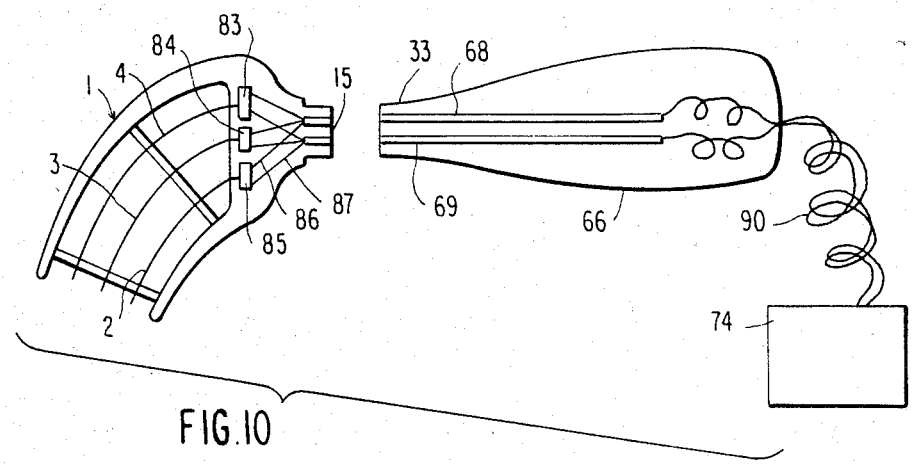
FIG. 10 is a diagramatic top view of a modified embodiment of the apparatus of the invention in which the brushes are driven by turbines.

In another modified embodiment as shown in FIG. 10, which also has a unitary housing 1, drive of the five brushes (only brushes 2, 3 and 4 are shown) is provided through five fluid-operated turbines (only three turbines 83, 84 and 85 are shown). These turbines may be fed by any pressure fluid (water, air, etc . . . ). Each turbine is connected to a fluid inlet nozzle and a fluid outlet nozzle. All the inlet and outlet nozzles merge, a the connecting ring 15, into two tubes which connect with two other tubes 68 and 69 extending from connecting part 33 of handle 66 to the inside of the latter to reach, e.g. via flexible hoses 90, a pressure fluid source 74. Source 74 may be, e.g. an electrically-operated pump or a system for connection to tap water feeder mains, capble to be connected, e.g. to a tap.

Figure 11:
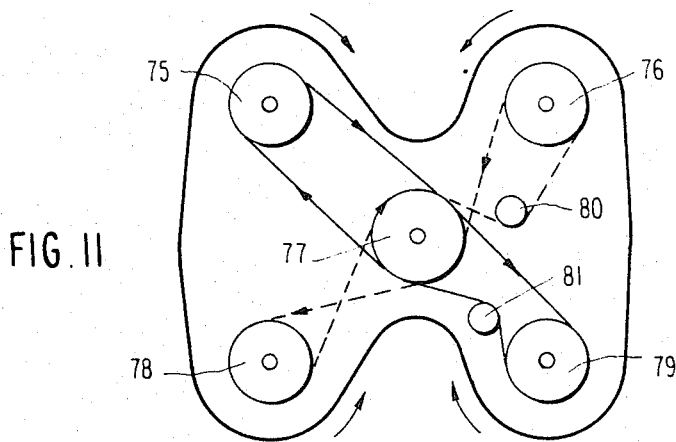
FIG. 11 shows a method of driving the brushes by pulleys and belts.

In the modified embodiment of FIG. 11, instead of the gear train of the embodiment of FIGS. 1 to 8 or of FIG. 9, there is shown a drive comprising five pulleys 75, 76, 77, 78 and 79 for rotating the five brushes, a pair of crossed belts cooperating with the center pulley as shown in FIG. 11 and two end pulleys. Two additionnal pulleys 80 and 81 maintain tension in the belts. Of course, there can be substituted any means equivalent to the belts such as strings, elastic bands, small chains, and the like.

So that the housing 1 is adaptable to dental arches having various configurations and sizes, the housing portion 1a, i.e. parts 10, 11, 13 and 14 are advantageously made from a relatively flexible material. On the other hand, housing portion 1b is made from a stiff material. Both materials may preferably be plastics.

The rotating brushes must have a flexible core which may consist, e.g. of a plastic rod or a tube of rubber-injected plastic. Such a core or hub may be reinforced with fiberglass and/or carbon fiber. The hair elements completely extend through the hubs.

An entire brush, i.e. the hub and hair, may also be integrally made from plastics such as polyamide.

In order to improve adaptability to dental arches having various configurations, brush may have hair elements of different lengths, such as alternating long and short hair elements.

Finally, so that a standard, single-sized apparatus for adults can be made, a length shorter (by one tooth length) than half that of the dental arches may be advantageously given to the brushes, such that the brushes can act upon teeth from the middle sagittal plane to the second molar. Thus, the flexibility of housing portion 1a enables users having longer dental arches to move the apparatus a slight rearward distance during the cleaning operation to brush all the teeth.

I claim:

1. A dental hygiene apparatus having a plurality of incurvated flexible rotating brushes for simultaneously cleaning the teeth of two opposed mandibles by brushing in a gum to tooth direction, said apparatus comprising a housing for mounting said brushes, said housing defining an open brush holder being shaped as an arcuate sector and having a length and incurvated shape matching that of two opposed half dental arches, said open brush holder portion including an inner tongue-guard and a cheek guard, said tongue-guard and said cheek guard being spaced apart by at least two transverse spacers, said plurality of brushes consisting of five incurvated brushes mounted in an H-shaped configuration on said spacers, said H-shape being formed by mounting each of four of said five brushes on said spacers at the four ends of said H-shaped configuration and by mounting the fifth of said five brushes at a center point of the horizontal leg of said H-shaped configuration, and means for simultaneously rotating said brushes, said housing including upper and lower restrictions defining a biting portion for receiving the upper and lower incisor teeth of the opposite two half dental arches to lock said apparatus in the mouth as said apparatus is bitten by the incisor teeth at said restrictions.

2. A dental hygiene apparatus as defined in claim 1 wherein each of said brushes includes a flexible rod mounted between said spacers and a plurality of brush hairs mounted on said rod along its length.

3. A dental hygiene apparatus as defined in claim 1 wherein said means for simultaneously rotating said brushes includes a rotatable gear rotating each of said brushes and a driving connection between said gear and the brush rotated by said gear.

4. A dental hygiene apparatus as defined in claim 3 whrein said means for simultaneously rotating said brushes includes a center rotatable gear for rotating the center brush of said H-shaped configuration of brushes, and a pair of gears on each side of said center gear, each of said pair of gears rotatably connected to one of the rotatable gears rotating each of said brushes on the legs of the H-shaped configuration of brushes, one of each of said pair of gears rotatably connected to the center gear and to the other gear of said pair of gears, and means for rotating said center gear and, in turn, imparting rotation to said pair of gears on each side of said center gear and to the gears rotating the brushes on each leg of the H-shaped configuration.

5. A dental hygiene apparatus as defined in claim 3 wherein said housing consists of two separate parts capable of being attached and detached from each other, said flexible rotating brushes being mounted in one part and said rotatable gear rotating each of said brushes being mounted in the other part of said housing.

6. A dental hygiene apparatus as defined in claim 4 wherein said housing consists of two separate parts capable of being coupled and uncoupled from each other, said flexible rotating brushes being mounted in one part and said gears being mounted in the other part of said housing.

7. A dental hygiene apparatus as defined in claim 6 wherein each of said gears for imparting rotation to said brushes has a flexible shaft connected to and extending from said gear to the coupling end of that portion of said housing, each of said flexible shafts being rotatably engaged with a brush when the two portions of the housing are coupled.

8. A dental hygiene apparatus as defined in claims 1, 2, 3, 4, 5, 6 or 7 in which said brush holder portion is constructed of a flexible material and said biting portion is constructed of a stiff material.

9. A dental hygiene apparatus as claimed in claims 1, 2, 3, 4, 5, 6 or 7 in which said brushes have hair elements of different lengths, alternating between long hair elements and short hair elements.

* * * * *